United States Patent
Stewart et al.

(10) Patent No.: US 8,096,959 B2
(45) Date of Patent: Jan. 17, 2012

(54) TRANS-SEPTAL CATHETER WITH RETENTION MECHANISM

(75) Inventors: Mark T. Stewart, Lino Lakes, MN (US); David E. Francischelli, Anoka, MN (US); James R. Skarda, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 1102 days.

(21) Appl. No.: 11/923,320

(22) Filed: Oct. 24, 2007

(65) Prior Publication Data

US 2008/0045898 A1 Feb. 21, 2008

Related U.S. Application Data

(62) Division of application No. 10/152,553, filed on May 21, 2002, now abandoned.

(60) Provisional application No. 60/292,483, filed on May 21, 2001.

(51) Int. Cl.
*A61B 17/88* (2006.01)

(52) U.S. Cl. .......... 600/585; 128/898; 607/99; 607/122; 607/128; 606/108; 604/264

(58) Field of Classification Search .................. None
See application file for complete search history.

(56) References Cited

U.S. PATENT DOCUMENTS

| | | |
|---|---|---|
| 3,952,742 A | 4/1976 | Taylor |
| 4,836,204 A | 6/1989 | Landymore |
| 5,312,341 A | 5/1994 | Turi |
| 5,690,611 A | 11/1997 | Swartz et al. |
| 5,897,553 A | 4/1999 | Mulier |
| 5,938,660 A | 8/1999 | Swartz |
| 5,971,983 A | 10/1999 | Lesh |
| 6,063,081 A | 5/2000 | Mulier |
| 6,079,414 A | 6/2000 | Roth et al. |
| 6,090,084 A | 7/2000 | Hassett et al. |
| 6,096,037 A | 8/2000 | Mulier |
| 6,132,438 A | 10/2000 | Fleischman et al. |
| 6,165,174 A | 12/2000 | Jacobs |
| 6,200,315 B1 | 3/2001 | Gaiser et al. |
| 6,239,393 B1 | 5/2001 | Mulier |

(Continued)

FOREIGN PATENT DOCUMENTS

WO W09404214 A 3/1994

(Continued)

OTHER PUBLICATIONS

International Search Report, PCT/US02/16142, May 12, 2002, 8 Pages.

*Primary Examiner* — Kennedy Schaetzle

(57) ABSTRACT

A trans-septal guide catheter for providing access through the septum separating a first heart chamber from a second heart chamber that includes an elongated guide catheter body extending between guide catheter proximal and distal ends. A distal segment of the guide catheter is adapted to be inserted through the septum to locate the distal segment of the guide catheter within one of the first heart chamber and the second heart chamber. The catheter body encloses a guide catheter lumen adapted to provide access into the one of the first heart chamber and the second heart chamber through a guide catheter lumen proximal end opening and a guide catheter lumen distal end opening. A retention mechanism engages the septum and maintains the distal segment of the guide catheter extending into the one of the first heart chamber and the second heart chamber.

9 Claims, 10 Drawing Sheets

U.S. PATENT DOCUMENTS

| | | | |
|---|---|---|---|
| 6,328,736 B1 | 12/2001 | Mulier |
| 6,358,248 B1 | 3/2002 | Mulier |
| 6,361,531 B1 | 3/2002 | Hissong |
| 6,409,722 B1 | 6/2002 | Hoey |
| 6,440,130 B1 | 8/2002 | Mulier |
| 6,443,952 B1 | 9/2002 | Mulier |
| 6,475,216 B2 | 11/2002 | Mulier |
| 6,488,680 B1 | 12/2002 | Francischelli |
| 6,502,575 B1 | 1/2003 | Jacobs |
| 6,514,250 B1 | 2/2003 | Jahns |
| 6,537,248 B2 | 3/2003 | Mulier |
| 6,537,272 B2 | 3/2003 | Christopherson |
| 6,558,382 B2 | 5/2003 | Jahns |
| 6,584,360 B2 | 6/2003 | Francischelli |
| 6,585,732 B2 | 7/2003 | Mulier |
| 6,610,060 B2 | 8/2003 | Mulier |
| 6,613,048 B2 | 9/2003 | Mulier |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,911,019 B2 | 6/2005 | Mulier |
| 6,916,318 B2 | 7/2005 | Francischelli |
| 6,936,046 B2 | 8/2005 | Hissong |
| 6,939,348 B2 | 9/2005 | Malecki |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0193147 A1 | 9/2004 | Malecki |
| 2004/0215183 A1 | 10/2004 | Hoey |
| 2004/0220560 A1 | 11/2004 | Briscoe |
| 2004/0230185 A1 | 11/2004 | Malecki |
| 2004/0236322 A1 | 11/2004 | Mulier |
| 2004/0243122 A1 | 12/2004 | Auth |
| 2004/0267191 A1 | 12/2004 | Hanson |
| 2004/0267326 A1 | 12/2004 | Ocel |
| 2005/0021016 A1 | 1/2005 | Malecki |
| 2005/0033280 A1 | 2/2005 | Francischelli |
| 2005/0033288 A1 | 2/2005 | Auth |
| 2005/0034735 A1 | 2/2005 | Deem |
| 2005/0080406 A1 | 4/2005 | Malecki |
| 2005/0090815 A1 | 4/2005 | Francischelli |
| 2005/0131401 A1 | 6/2005 | Malecki |
| 2005/0131460 A1 | 6/2005 | Hanson |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

FOREIGN PATENT DOCUMENTS

| | | |
|---|---|---|
| WO | WO 9918870 A | 4/1999 |
| WO | WO 9918871 A | 4/1999 |

TRANS-SEPTAL CATHETER WITH RETENTION MECHANISM

REFERENCE TO PRIORITY APPLICATIONS

This application is a divisional of U.S. application Ser. No. 10/152,553, filed May 21, 2002 now abandoned, which claims priority to U.S. provisional application No. 60/292,483, filed May 21, 2001, both of which are incorporated herein by reference in their entirety.

FIELD OF THE INVENTION

The present invention relates generally to trans-septal introducers or guide catheters adapted to introduce an instrument through the septum between a left and right heart chamber, and more particularly, the present invention relates to a trans-septal guide catheter having a retention mechanism for retaining the distal end of the guide catheter within the left heart chamber particularly to enable passage therethrough of an electrophysiology (EP) catheter.

BACKGROUND OF THE INVENTION

The heart includes a number of pathways through which electrical signals necessary for normal, electrical and mechanical synchronous function of the upper and lower heart chambers propagate. Tachycardia, that is abnormally rapid rhythms of the heart, is caused by the presence of an arrhythmogenic site or accessory pathway, which bypasses or short circuits the nodal pathways in the heart. Tachycardias may be categorized as ventricular tachycardias (VTs) or supraventricular tachycardias (SVTs). The most common SVTs include atrioventricular nodal reentrant tachycardia (AVNRT), Atrioventricular reentrant tachycardia (AVRT), atrial fibrillation (AF), and atrial flutter (AFI). Reentrant tachycardias originate in the atria and are typically caused by an accessory pathway or inappropriate premature return excitation from the ventricle through the AV node or left sided accessory pathway. Conditions such as AF and AFI involve either premature excitation from focal ectopic sites within the atria or excitations coming through inter-atrial reentry pathways as well as regions of slow conduction within the atria. VTs originate from within the ventricles and have their entire circuit contained within the ventricles. These VTs include bundle branch reentrant tachycardia (BBR), right ventricular outflow tract tachycardia (RVOT), and ventricular fibrillation (VF). VTs are often caused by arrhythmogenic sites associated with a prior myocardial infarction as well as reentrant pathways between the ventricles. BBR involves an inappropriate conduction circuit that uses the right and left bundle branches. RVOT can be described as a tachycardia originating from the right ventricular outflow tract, which involves ectopic triggering or reentry mechanisms. VF is a life threatening condition where the ventricles entertain a continuous uncoordinated series of contractions that cause a cessation of blood flow from the heart. If normal sinus rhythm is not restored, the condition is terminal.

Treatment of both SVTs and VTs may be accomplished by a variety of approaches, including drugs, surgery, implantable electrical stimulators, and catheter ablation of cardiac tissue of an effected pathway. While drugs may be the treatment of choice for many patients, drugs typically only mask the symptoms and do not cure the underlying cause. Implantable electrical stimulators, e.g., pacemakers, afferent nerve stimulators and cardioverter/defibrillators, which have proven to provide successful treatment, usually can only correct an arrhythmia after it occurs and is successfully detected. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radio frequency (RF) electrical energy, laser energy, ultrasound, microwaves, and the like.

RF ablation protocols have proven to be highly effective in treatment of many cardiac arrhythmias while exposing the patient to minimum side effects and risks. RF catheter ablation is generally performed after an initial electrophysiologic (EP) mapping procedure is conducted using an EP mapping catheter to locate the arrhythmogenic sites and accessory pathways. After EP mapping is completed, an RF ablation catheter having a suitable electrode is introduced to the appropriate heart chamber and manipulated so that the electrode lies proximate the target tissue. Such catheters designed for mapping and ablation, frequently include one or more cylindrical or band-shaped individual electrodes mounted to the distal section of the catheter so as to facilitate mapping of a wider area in less time, or to improve access to target sites for ablation. RF energy is then applied through the electrode(s) to the cardiac tissue to ablate a region of the tissue that forms part of the arrhythmogenic site or the accessory pathway.

Such mapping and ablation catheters are inserted into a major vein or artery, usually in the neck or groin area, and guided into the chambers of the heart by appropriate manipulation through a venous or arterial route, respectively. The catheter must have a great deal of flexibility or steerability to be advanced through the vascular system into a chamber of the heart, and the catheter must permit user manipulation of the tip even when the catheter body traverses a curved and twisted vascular access pathway. Such catheters must facilitate manipulation of the distal tip so that the distal electrode(s) can be positioned and held against the tissue region to be mapped or ablated.

The arrhythmogenic sites or accessory pathways to be mapped and ablated frequently occur within the left atrial wall, particularly around pulmonary vein orifices. It is preferable in such cases to introduce an instrument into the right atrium by a venous route including the inferior vena cava and to advance it through the septum separating the right and left atrium. In one exemplary approach, a guide catheter is inserted in this manner into the right atrium, and instruments are introduced through the guide catheter lumen that are manipulated from their proximal end and advanced through the septal wall first creating a very small trans-septal perforation, and then enlarging the perforation by dilation or the like. The guide catheter is then advanced over the instruments or advanced directly through the perforation in the septal wall to locate the guide catheter distal end within the left atrial chamber. The penetrating instruments are retracted from the guide catheter lumen. The proximal end of the guide catheter is typically taped to the patient's body or a support to inhibit retraction back into the right atrial chamber. The mapping and ablation catheters are then inserted through the guide catheter lumen to locate their distal segments within the left atrial chamber.

The mapping and ablation procedures are undertaken, the mapping and ablation catheters are retracted, and the guide catheter is also retracted. The trans-septal perforation tends to shrink as the dilated myocardial tissue expands across the perforation.

It is important that the distal segment of the guide catheter inserted through the septum remain in place for the entire procedure and not slip back into the right atrium. The guide catheter can be inadvertently dislodged by movements of the proximal segment emerging from the site of incision. The dislodgement can require withdrawal of the instruments in use, jeopardizing their sterility, while delay occurs in reestablishing catheter position and resumption of the procedure.

In addition, the only way to monitor the location of the distal segment of the guide catheter is through visualization of a radiopaque marker of the guide catheter in regard to recognizable physiologic features of the heart.

It is sometimes necessary that the distal end segment of the electrophysiology catheter be directed at an acute angle just as it exits the guide catheter lumen to be directed toward certain features of the left atrium. Therefore, only a very short distal segment of the guide catheter is extended into the left atrium past the septum so that the electrophysiology catheter can be directed to the feature of interest. It is more difficult to maintain the distal segment within the left atrium as the distal segment within the left atrium is shortened.

There is therefore a need for a guide catheter that does not readily retract through the septum once it has been extended through the septum.

SUMMARY OF THE INVENTION

The present invention is directed to an improved trans-septal guide catheter that can be passed through a septum from one heart chamber to another heart chamber and that possesses a retention mechanism for maintaining a distal segment thereof in the other heart chamber. For example, the trans-septal guide catheter can be introduced into the right atrium, passed through the atrial septum into the left atrium to locate a distal segment thereof within the left atrium, and retained within the left atrium so that the distal segment does not readily retract through the septum into the right atrium.

The trans-septal guide catheter provides access through the septum separating a right heart chamber from a left heart chamber and preferably includes an elongated guide catheter body extending between guide catheter proximal and distal ends enclosing a guide catheter lumen adapted to provide access into the left heart chamber through a guide catheter lumen proximal end opening and a guide catheter lumen distal end opening. Retention mechanisms are provided for engaging the septum and inhibiting retraction through the septum of the distal segment of the guide catheter extending into the left heart chamber. The trans-septal guide catheter particularly enables passage of an EP catheter through the guide catheter lumen for use in mapping and/or ablation of accessory pathways in myocardial tissue of the left atrial heart wall.

In one embodiment, the retention mechanism further includes at least one flexible, pliant, tine extending outwardly from a tine attachment with the distal segment of the guide catheter body to a tine free end. The tine free end is adapted to deflect inward toward the guide catheter body when restrained during advancement of the guide catheter and to extend further outward from the guide catheter body when restrained against the septal wall when any retraction force is applied to the guide catheter tending to retract the distal segment of the guide catheter body back into the right heart chamber.

In another embodiment, the retention mechanism includes an inflatable balloon inflated and deflated through an inflation and deflation lumen within the guide catheter body extending from a proximal inflation port at the guide catheter proximal end to a balloon inflation port within the inflatable balloon. The inflation medium is introduced through the balloon inflation and deflation lumen to inflate the balloon after the balloon is advanced through the septum into the left heart chamber. The inflated balloon bears against the septal wall and inhibits retraction through the septum of the distal segment of the guide catheter extending into the left heart chamber.

In still another embodiment, the retention mechanism includes a wire that is extendable through a wire deployment lumen of the catheter body. A distal wire segment has a non-straight configuration when extended out of the deployment lumen end opening and into engagement with the septal wall of the septum within the left heart chamber that inhibits retraction through the septum of the distal segment of the guide catheter extending into the left heart chamber and is straightened when advanced through the wire deployment lumen.

The non-straight configuration of the retention wire can include a wire coil formed of a plurality of wire turns of a coil, e.g., a planar coil, or an acute bend in the wire. The retention wire can be formed of a shape memory alloy to possess superelasticity that enables straightening of the non-straight configuration within the wire deployment lumen.

The guide catheters of the present invention solve the problem of maintaining the distal segment thereof in the heart chamber that the distal segment is introduced into and enables shortening of the length of the distal segment to enable maximal access to features of the heart chamber, particularly the left atrium. The retention mechanisms ensure that vent ports in the sidewall of the guide catheter body distal segment are within the heart chamber that the distal segment is introduced into and are not obstructed by the septum.

The retention mechanisms are preferably located to be deployed or self deploy in the heart chamber that the distal segment is introduced into to inhibit retraction when retraction force is applied to the guide catheter proximal end drawing the retention mechanism against the septal wall. It will be understood that the deployment mechanisms can be deployed more proximally to the guide catheter body distal segment to bear against the septal wall when advancement force is applied to the guide catheter proximal end. Slight force can then be applied to hold the catheter in position without advancing the guide catheter further into the accessed heart chamber. Moreover, it would be possible to duplicate the retention mechanism to deploy a retention mechanism on either side of the septum.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent from the following description in which the preferred embodiments are disclosed in detail in conjunction with the accompanying drawings in which.

DETAILED DESCRIPTION OF THE PREFERRED EMBODIMENTS

Figure 1:
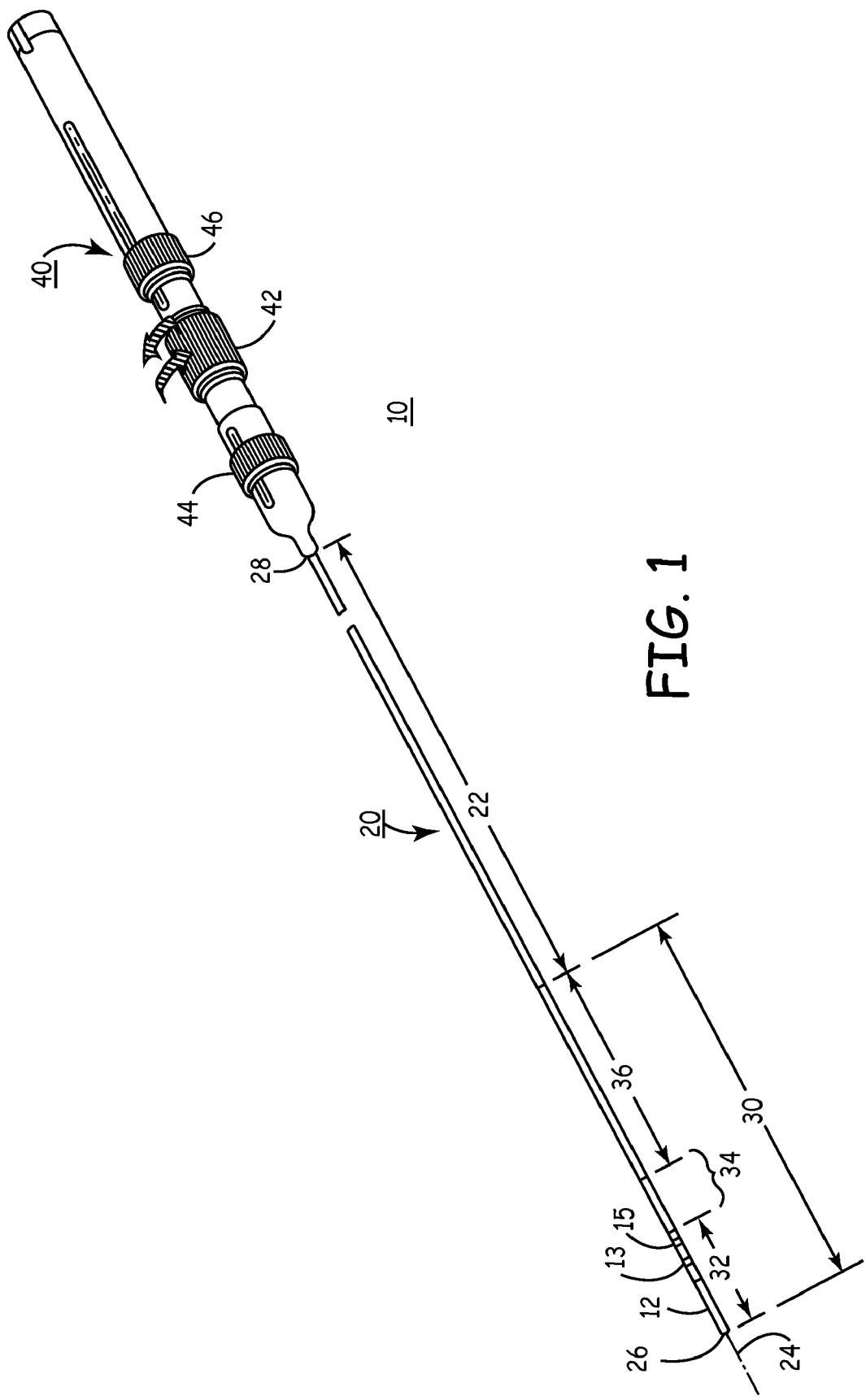
FIG. 1 is an overall view of one embodiment of an ablation and/or EP mapping catheter that can be passed through a guide catheter of the present invention.

FIG. 1 schematically illustrates an anatomically-conforming, multi-curve ablation and/or EP mapping catheter 10 that can be introduced through a guide catheter of the present invention for orienting a distal tip electrode 12 (or electrodes) with respect to the heart wall for RF ablation and/or EP mapping. The multi-curve catheter 10 can incorporate a porous tip and catheter lumen for emitting irrigating fluid around the distal tip electrode 12, but those features are not illustrated in FIG. 1 to simplify illustration. Moreover, the distal segment 32 is simplified in FIG. 1 to show an elongated tubular shaped ablation electrode 12 and a pair of mapping electrodes 13 and 15 in the illustration of FIG. 1, but the distal segment 32 may include a plurality of ring-shaped electrodes, one or more coil electrode or the like having other shapes that are presently used or may come into use and including several variations described below in reference to other figures including visible or invisible light, infrared, and electrical energy from or along the distal tip.

The catheter 10 includes a catheter shaft or body 20 and a handle 40. The catheter shaft or body 20 has a shaft axis 24 and extends between a distal end 26 and a proximal end 28 and is separated into a proximal section 22 and a distal section 30. Catheter body 20 may be of any suitable diameter and length and may be straight or pre-curved along its length, but preferably is straight when unrestrained. The distal section 30 or the distal segment thereof can be tapered from the diameter of the proximal section 22. Preferably, the catheter body 20 has a uniform outside diameter of about 0.052 inch (1.32 mm) to 0.1040 inch (2.64 mm) and a length of about 50 cm to 110 cm.

The proximal section 22 has sufficient column strength and is capable of good torque transmission to permit controlled placement of the distal section 30 at a target site in the heart including a selected cardiac valve or vessel in the manners discussed below. The distal section 30 is deflectable away from shaft axis 24 and includes a distal segment 32, a curvable proximal segment 36 having a proximal segment length, and a bendable intermediate segment 34 having an intermediate segment length disposed between the distal segment 32 and the curvable proximal segment 36. The illustrative tip electrode 12 is positioned along the distal segment 32, preferably extending proximally from the catheter body distal end 26 through all or part of the length of the distal segment 32. The distal segment 32 can include an elongated ablation electrode 12 that may be solid or irrigated and can include one or more proximal ring electrodes 13, 15 for use in mapping that are either located proximally as shown or distally from ablation electrode 12. Each electrode is separately connected to insulated conductors extending proximally through the catheter body 20 to terminals of a cable connector in or on the handle 40 that is connected via a cable to the ablation energy source and/or mapping signal amplifiers. As described further below, a thermocouple is also typically included in the distal segment 32 of such ablation catheters, and separately insulated thermocouple conductors extending proximally through the catheter body 20 to terminals of the cable connector in or on the handle 40 that are coupled via a cable to the temperature display and ablation energy control apparatus known in the art.

The handle 40 can take any of the forms known in the art for making electrical connections with the conductors within the catheter body 20, for delivering irrigation fluid to an irrigation lumen (if present) of the catheter body 20. The handle 40 also includes a mechanism for deflecting the distal tip section 30 into the shapes provided by the present invention. The mechanism can take any form for pulling, pushing and/or twisting the deflection or push/pull wires within the catheter body 20 as described further below. In the illustrated embodiment, the handle 40 is attached to the catheter body proximal end 28 and supports axially slidable manipulators comprising push-pull rings 44 and 46 and a rotatable lateral deflection ring 42 that are coupled to the proximal ends of a curve deflection push-pull wire, a knuckle deflection push-pull wire, and a lateral deflection wire identified and described further below. The lateral deflection ring 42 can be rotated to impart a torque in a lateral deflection wire coupled thereto to laterally rotate the distal section 30 with respect to axis 24 within the proximal section 22.

As shown in FIG. 1, when the push-pull wires are relaxed, the distal segment 32, the bendable intermediate segment 34, and the curvable proximal segment 36 are aligned with the shaft axis 24 that is referenced as 0°. The knuckle deflection push-pull wire can be retracted or pulled by sliding ring 46 proximally to impart a small radius bend from substantially 0°, wherein the distal and proximal segments 32 and 36 are axially aligned, to substantially 180°, whereby the distal and proximal segments 32 and 36 are substantially in side-by-side alignment. The knuckle deflection push-pull wire can be extended or pushed by sliding push-pull ring 46 distally to impart a small radius bend from substantially 0° to about −90°, that is in a bend direction opposite to the bend direction imparted when the knuckle deflection push-pull wire is retracted or pulled by sliding ring 46 proximally. The intermediate segment 34 is bent in a bending radius of between 2.0 mm and 7.0 mm, and preferably less than about 5.0 mm within the bending angle range. The abrupt knuckle bend angle range can be restricted further by positioning of the slide end stops for the push-pull ring 46 during assembly.

The manipulator push-pull ring 44 can be moved proximally or distally to move the curve deflection push-pull wire coupled thereto proximally or distally to form a curve in the proximal segment 36 that is opposed to or in the same direction as the bend imparted in the intermediate segment 34. The bend or curve of the proximal segment 36 that can be induced relative to the catheter body axis 24 as depicted in the figures can be between −90° to +270° relative to the proximal section 22. The curvature range of the proximal segment 36 can be restricted further by position of the slide end stops for the push-pull ring 44 during assembly.

Many possible co-planar curves induced in the segments of the distal section 30 in relation to the catheter body axis 24 accomplished by selective movement of the axially slidable manipulator rings 46 and 44 coupled to the knuckle deflection push-pull wire 56 and the curve deflection push-pull wire 54, respectively. The distal end of the knuckle deflection push-pull wire 56 terminates at the junction of the intermediate segment 34 with the distal segment 32, and the curve deflection push-pull wire 54 terminates at the junction of the intermediate segment 34 with the proximal segment 36. The knuckle deflection push-pull wire 56 and the curve deflection push-pull wire 54 extend in parallel with and are radially aligned to the catheter body axis 24 along a common radius extending from the catheter body axis 24 through the proximal section 22 and the proximal segment 36. The knuckle deflection push-pull wire 56 is spaced further away from the axis 24 than the curve deflection push-pull wire 54 through the proximal section 22 and proximal segment 36. The distal section of the knuckle deflection push-pull wire 56 traversing the intermediate segment 34 is axially aligned with the axis of the curve deflection push-pull wire 54 in the proximal segment 36.

When the ring 42 is rotated clockwise or counterclockwise, the lateral deflection wire is twisted, causing the junction of the proximal and intermediate segments 36 and 34 to rotate. It will be understood from the construction of the lateral deflection wire described below that a lateral deflection of the tip segment 32 and the intermediate segment 34 in the range of −90° to +90° with respect to catheter body straight axis 24 can be achieved by such rotation.

The structure of the catheter body 20 that achieves these angular tip section deflections and the lateral deflection is illustrated in commonly assigned U.S. patent application Ser. No. 09/685,193, filed Oct. 10, 2000, in the names of Mark T. Stewart et al. for HEART WALL ABLATION/MAPPING CATHETER AND METHOD. The guide catheter of the present invention is advantageously employed with this and other ablation and/or EP mapping catheters that are introduced into through the guide catheter lumen that is itself extended from the right atrium through the septum to locate a distal segment of the guide catheter therein as shown in FIG. 2, for example.

Figure 2:
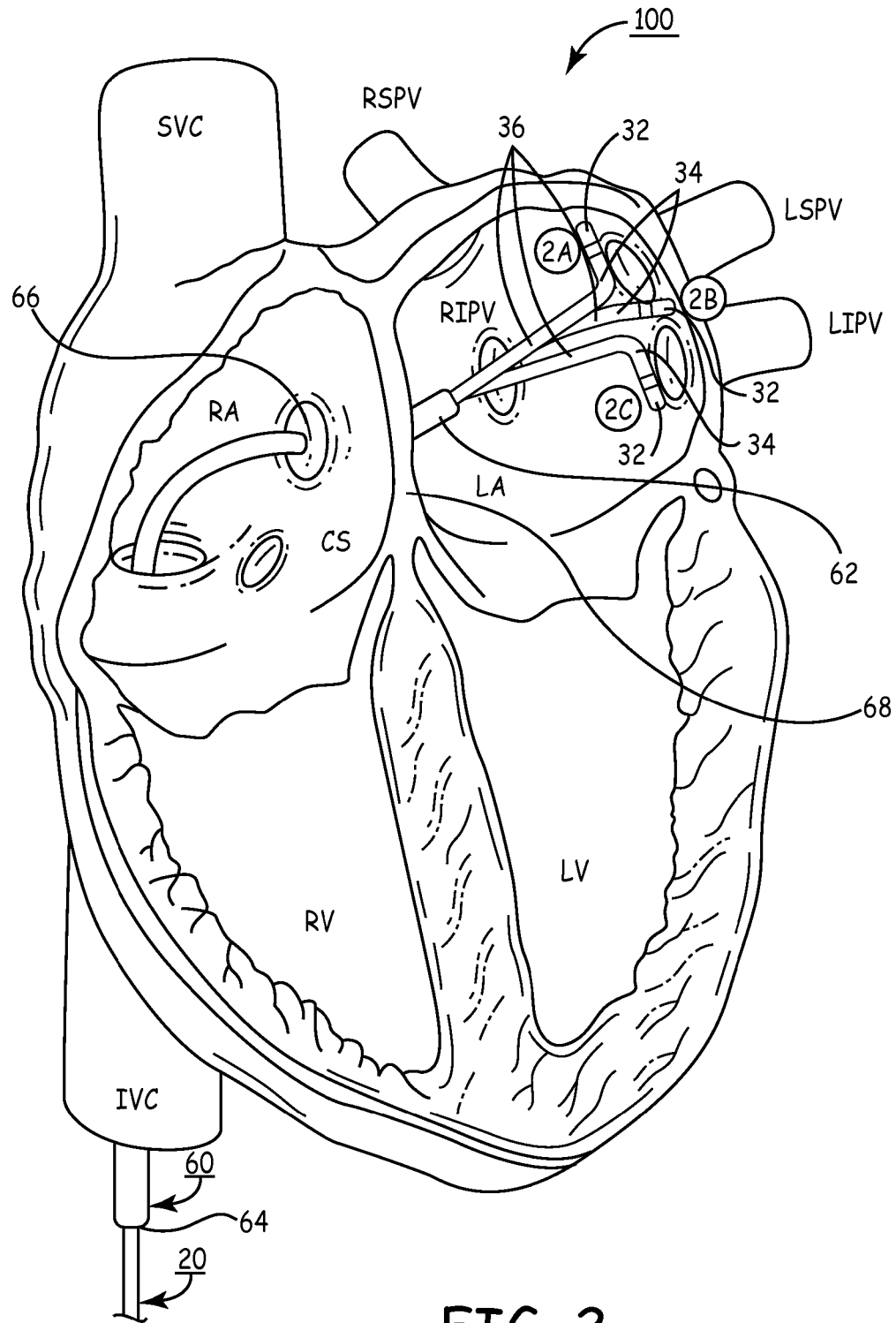
FIG. 2 is a schematic illustration of the introduction of the ablation and/or EP mapping catheter distal section into the left atrium through the lumen of a guide catheter extending through an incision or perforation through the septum between the right and left atrium.

FIG. 2 is a schematic illustration of the introduction of the ablation and/or EP mapping catheter distal section into the left atrium through the lumen 64 of a guide sheath or catheter 60 extending through an incision or perforation through the septum to locate a guide catheter distal segment 62 within the left atrium. FIG. 2 illustrates, in simplified form, a sectioned heart 100 and the major vessels bringing venous blood into the right atrium RA, oxygenated blood into the left atrium (LA) and the aorta and aortic arch (FIG. 20) receiving oxygenated blood from the left ventricle (LV). The venous blood is delivered to the RA through the superior vena cava (SVC), the inferior vena cava (IVC) and the coronary sinus (CS) which all open into the right atrium (RA) superior to the annulus of the tricuspid valve leading into the right ventricle. Oxygenated blood from the two lungs is delivered into the left atrium by the left and right, inferior and superior, pulmonary veins (LIPV, LSPV, RIPV and RSPV) which are superior to the mitral valve. The RA and LA are separated by an inter-atrial septum 68, and the RV and LV are separated by a ventricular septum. The tricuspid valve and mitral valve are not shown completely to simplify the figures.

Accessory pathways develop in several parts of the RA and LA that are reached by the catheter 10 to be mapped and/or ablated in accordance with methods of use thereof. Premature activations that cause atrial fibrillation occur frequently in the LA wall, particularly from pulmonary venous foci around the annular orifices of certain or all of the pulmonary veins RIPV, RSPV, LIPV, LSPV shown in FIG. 2. The LA can be accessed in a retrograde manner through the aorta. However, another convenient approach to the LA is via a puncture or perforation made through the inter-atrial septum from the RA. The trans-septal guide sheath or catheter 60 depicted in FIG. 2 is inserted through the septum 68 via the perforation 66.

The EP mapping/ablation catheter 20 is introduced through the guide catheter lumen 64, and the handle is manipulated to form the distal section 30 with about a +90° knuckle bend made in the intermediate segment and slight positive, neutral or negative curvatures in the range of about −45° to +45° in the proximal segment 36 to align the distal tip to locations 2A, 2B or 2C. Continuous lesions can be made around the selected pulmonary valve orifice by successively moving the distal electrode to the next location and applying RF ablation energy. The movement can be effected by twisting the distal segment about the catheter body axis using the deflection wire and manipulator.

These manipulations can require that the length of the guide catheter distal segment 62 be minimized and can cause inadvertent retraction of the distal segment 62 through the perforation 66 in the septal wall 68 and into the RA. The guide catheters of the present invention are formed with a retention mechanism that is deployed to bear against the LA wall around or alongside the perforation 66. The perforation 66 is first formed through the septal wall of the septum 68, a distal segment of the guide catheter is advanced into the right heart chamber. In this particular case, the guide catheter is advanced through the IVC into the RA and then through the perforation 66 to locate the distal segment in the LA. Then, the retention mechanism is deployed or self deploys into engagement with the septum 68 to inhibit retraction of the distal segment of the guide catheter through the perforation 66 back into RA when any retraction force is applied to the guide catheter. In this way, access is provided to introduce instruments or materials into the LA. The preferred use of the guide catheter of the present invention is to introduce a mapping/ablation EP catheter of the type depicted in FIGS. 1 and 2, for example, into the LA. Then, the deployment mechanism is withdrawn or retracted or overcome by applied retraction force to enable withdrawal of the guide catheter through the perforation 66.

Figure 3:
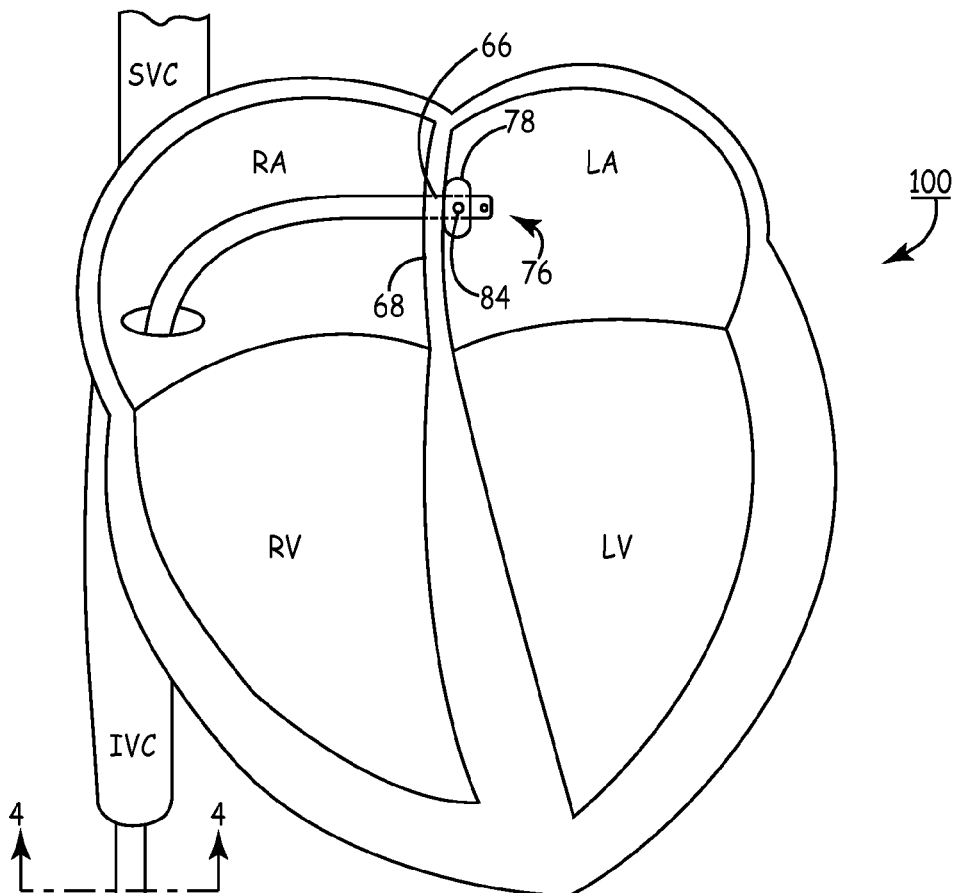
FIG. 3 is a simplified schematic illustration of a first embodiment of a guide catheter of the present invention having a deployable retention mechanism comprising an expandable balloon expanded in the left atrium and drawn against the septal wall in the left atrium to inhibit retraction of the guide catheter distal segment into the right atrium.
Figure 4:
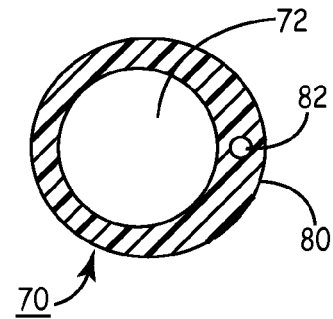
FIG. 4 is a cross-section view along lines 4-4 of FIG. 3 depicting the guide catheter lumen and balloon inflation/deflation lumen.

FIG. 3 is a simplified schematic illustration of a first embodiment of a guide catheter 70 of the present invention having a deployable retention mechanism comprising an expandable balloon 78 expanded in the LA and drawn against the septal wall in the LA of the septum 66 to inhibit retraction of the guide catheter distal segment 76 into the RA. FIG. 4 is a cross-section view along lines 4-4 of FIG. 3 depicting the guide catheter lumen 72 and balloon inflation/deflation lumen 82 within the guide catheter body 80.

The inflatable balloon 78 is inflated and deflated through the inflation/deflation lumen 82 that extends within the guide catheter body 80 from a proximal inflation port 86 at the guide catheter proximal end 74 to a balloon inflation port 84 within the inflatable balloon 78. The inflation medium (preferably a fluid, e.g., saline or a radiopaque solution) is introduced through the balloon inflation/deflation lumen 82 to inflate the balloon 78 after the deflated balloon 78 is advanced through the septum 68 into the LA. The inflated balloon 78 bears against the septal wall and resists or inhibits retraction through the septum 66 of the distal segment 76 of the guide catheter 70 extending into the LA. The mapping/ablation EP catheter can then be introduced through the guide catheter lumen 72 as depicted in FIG. 2 to map or ablate cardiac tissue.

It may be noted that guide catheter 70 may include a second expandable balloon 78a (shown dashed) that is adapted to be expanded in the RA and drawn against the septal wall. This is discussed further below.

Figure 5:
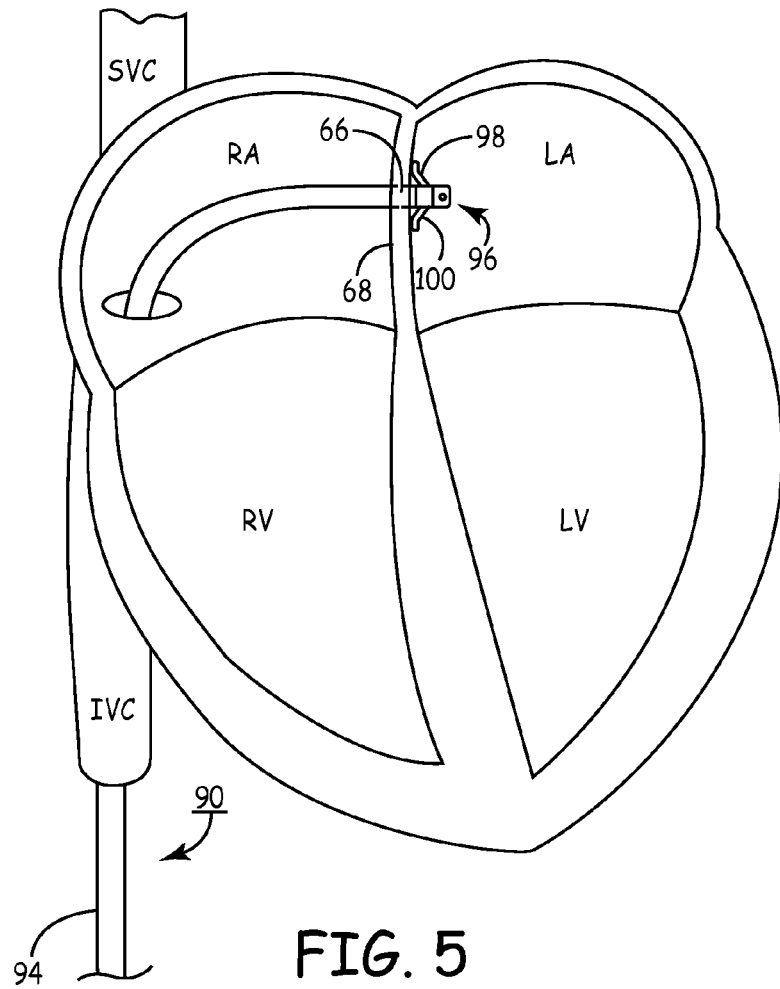
FIG. 5 is a simplified schematic illustration of a second embodiment of a guide catheter of the present invention having a retention mechanism comprising a plurality of pliant tines drawn against the septal wall in the left atrium to inhibit retraction of the guide catheter distal segment into the right atrium.
Figure 6:
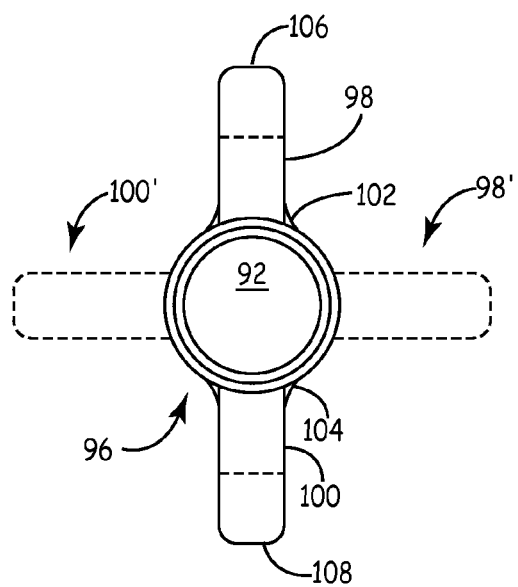
FIG. 6 is an end view of the distal segment of the guide catheter of FIG. 5 depicting the guide catheter lumen and outwardly extending tines.

FIG. 5 illustrates a second embodiment of a guide catheter 90 of the present invention having a self deployed retention mechanism that includes a plurality of pliant tines 98, 100 drawn against the septum in the LA to inhibit retraction of the guide catheter distal segment 96 through the perforation 66 into the RA. FIG. 6 is an end view of the distal segment 96 of the guide catheter of FIG. 5 depicting the guide catheter lumen 92 and outwardly extending tines 98 and 100.

Each such flexible, pliant, tine 98, 100 extends outwardly from a tine attachment 102, 104 with the distal segment of the guide catheter body to a respective tine free end 106,108. Preferably, the flexible, pliant, tines 98, 100 extend proximally and outwardly from the respective tine attachments 102, 104 with the guide catheter body 94 at an acute angle to the guide catheter body 94. The tines 98, 100 can be rectangular or circular in cross-section and can be thinner or thicker than depicted and longer or shorter than depicted. The tines 98, 100 can be formed of a plastic material, polyurethane or silicone rubber.

The tine free ends 106 and 108 are able to deflect inward toward the guide catheter body 94 by contact against the septum 68 when the guide catheter 90 is advanced through the perforation 66. The tines 98, 100 extend or spread further outward from the guide catheter body 94 against the septal wall as shown in FIG. 5 when any retraction force is applied to the guide catheter 90 tending to retract the distal segment 96 of the guide catheter body back into the RA. While the tines 98, 100 resist bending to extend distally, they can be inverted if sufficient retraction force is applied to the guide catheter body 94 at its proximal end in order to retract the distal segment 96 through the perforation 66.

It will be understood that more than one tine can be employed arrayed around the circumference of the catheter body 94. Two additional tines 98' and 100' are illustrated in broken lines in FIG. 6 to illustrate four tines in this instance. The additional tines 98', 100' are formed and function in the same manner as tines 98, 100 as described above.

Figure 7:
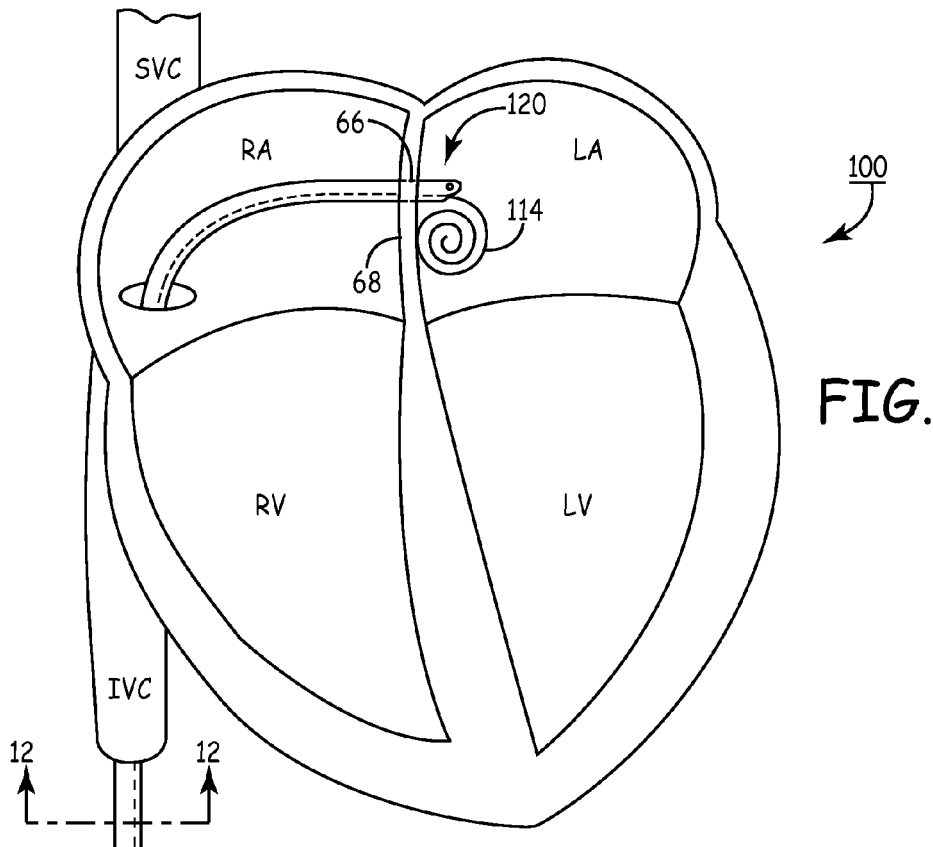
FIG. 7 is a simplified schematic illustration of a third embodiment of a guide catheter of the present invention having a deployable retention mechanism comprising an extendable wire that forms a wire coil when extended from a wire deployment lumen into the left atrium and inhibits retraction of the guide catheter distal segment into the right atrium.
Figure 12:
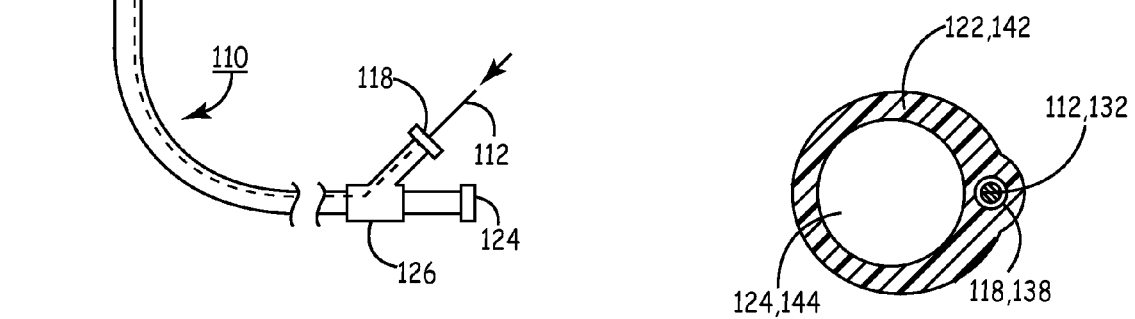
FIG. 12 is a cross-section view along lines 12-12 of FIGS. 7-10 depicting the guide catheter lumen and one embodiment of the extendable wire lumen and extendable wire cross-section.
Figure 8:
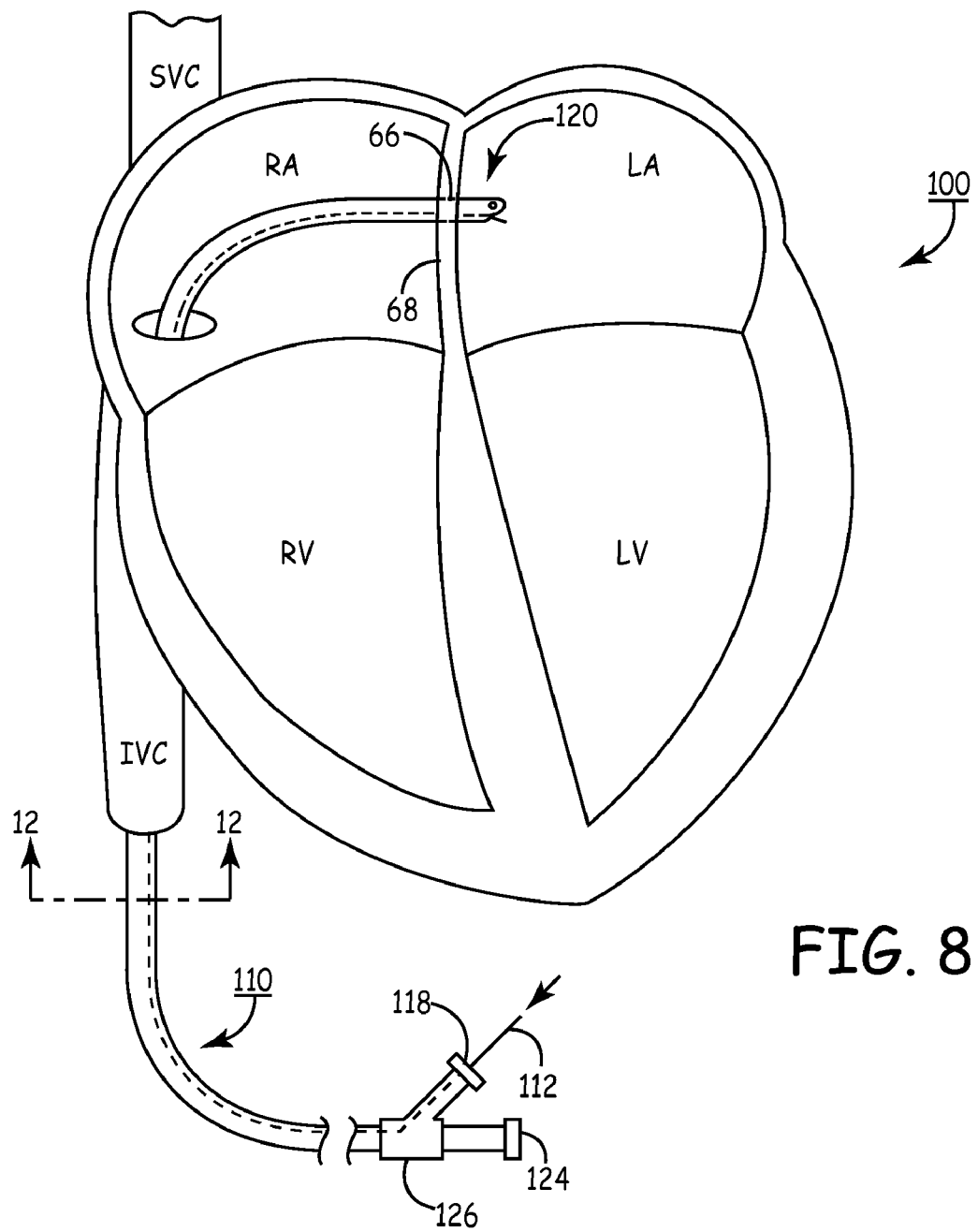
FIG. 8 is a simplified schematic illustration of the third embodiment of a guide catheter of the present invention showing the extendable wire that forms the wire coil when extended into the left atrium retracted into the wire deployment lumen during introduction or withdrawal of the distal segment through the septum into or from the left atrium.

FIG. 7 illustrates a third embodiment of a guide catheter 110 of the present invention having a deployable retention mechanism that includes an extendable wire 112 that forms a wire coil 114 when extended from a wire deployment lumen 118 (shown in FIG. 12) into the LA and inhibits retraction of the guide catheter distal segment 116 into the RA. The catheter body 122 encloses a guide catheter lumen 124 (FIG. 12) adapted to receive a mapping/ablation EP catheter and the wire deployment lumen 118 extending between a deployment lumen proximal end opening and a deployment lumen distal end opening in the distal segment 120. FIG. 8 shows the extendable wire 112 that forms a wire coil 114 when extended into the LA retracted into the wire lumen 118 during introduction into or withdrawal from the RA of the distal segment 116 through the perforation 66 in the septum 68.

In use, the elongated retention wire 112 is extended at guide catheter proximal end 126 through the wire deployment lumen 118 to dispose the distal wire segment 114 within the LA as shown in FIG. 7. The distal wire segment 114 is straightened when advanced through the wire deployment lumen 118 but forms a non-straight configuration when extended out of the deployment lumen end opening and into engagement with the septal wall of the septum 68 within the LA that inhibits retraction through the septum of the distal segment 120 extending into the LA. The mapping/ablation EP catheter can then be introduced through the guide catheter lumen 124 as depicted in FIG. 2 to map or ablate cardiac tissue. When the procedure is completed, the elongated retention wire 112 is retracted as shown in FIG. 8 to enable retraction of the guide catheter distal segment 120 back into the RA.

The retention wire 112 and wire lumen 118 can have a circular or rectangular cross-section, and the wire coil 114 can be any desired non-straight configuration, e.g., a wire coil formed of a plurality of wire turns wound in a common plane as shown or into any other coil shape. The retention wire 112 can be formed of a shape memory alloy that possesses superelasticity that enables straightening of the non-straight configuration within the wire deployment lumen 118.

Figure 9:
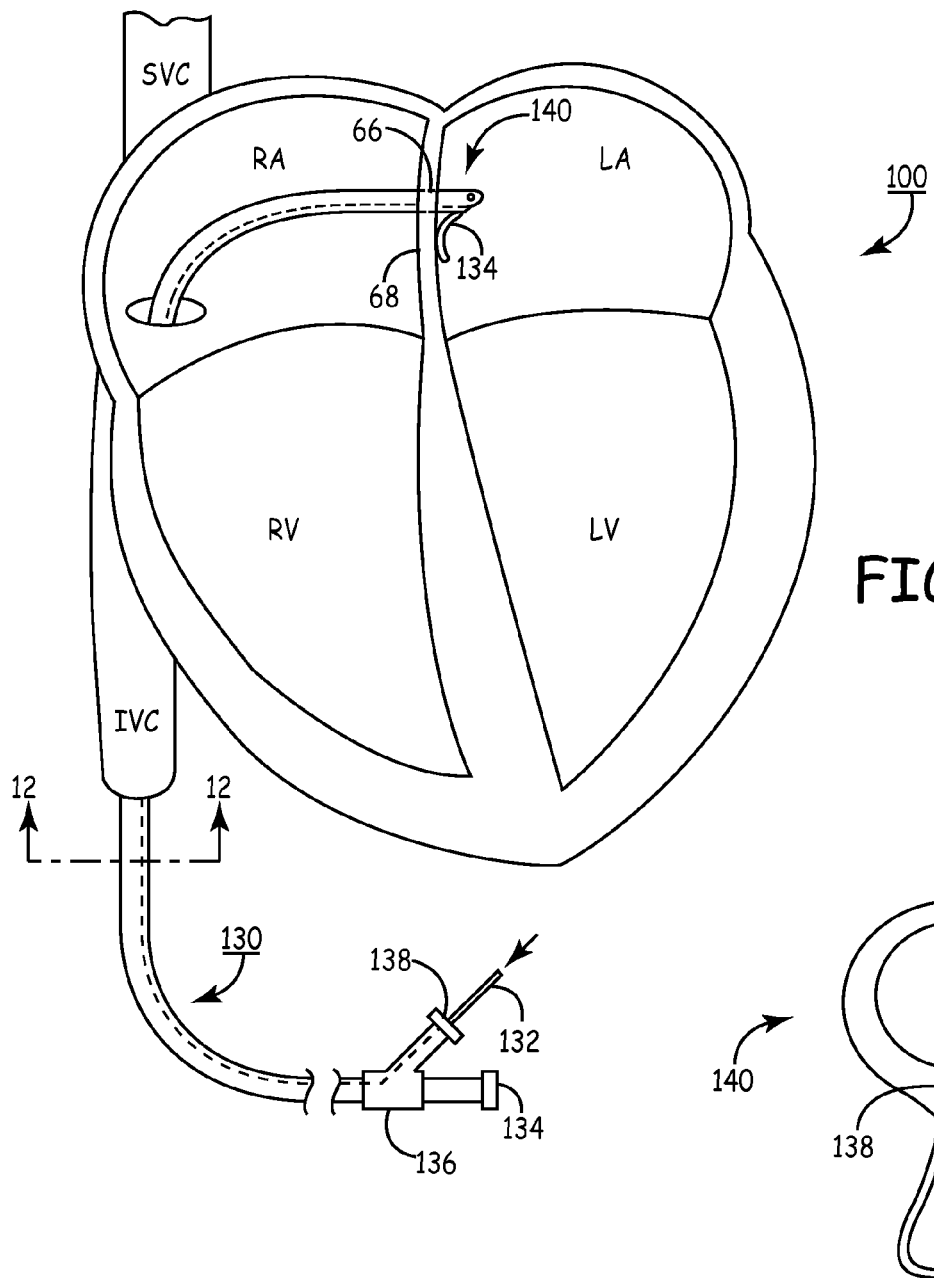
FIG. 9 is a simplified schematic illustration of a fourth embodiment of a guide catheter of the present invention having a deployable retention mechanism comprising an extendable wire that bends over at an acute angle when extended from a wire lumen into the left atrium and inhibits retraction of the guide catheter distal segment into the right atrium.
Figure 11:
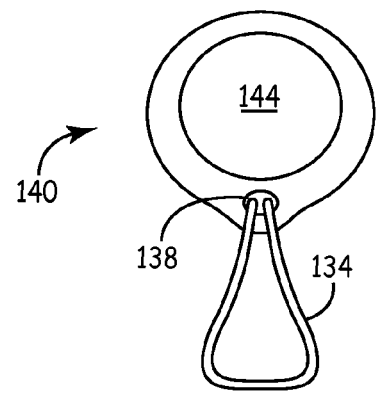
FIG. 11 is an expanded view of the distal end segment of the extendable wire of FIGS. 9 and 10.
Figure 10:
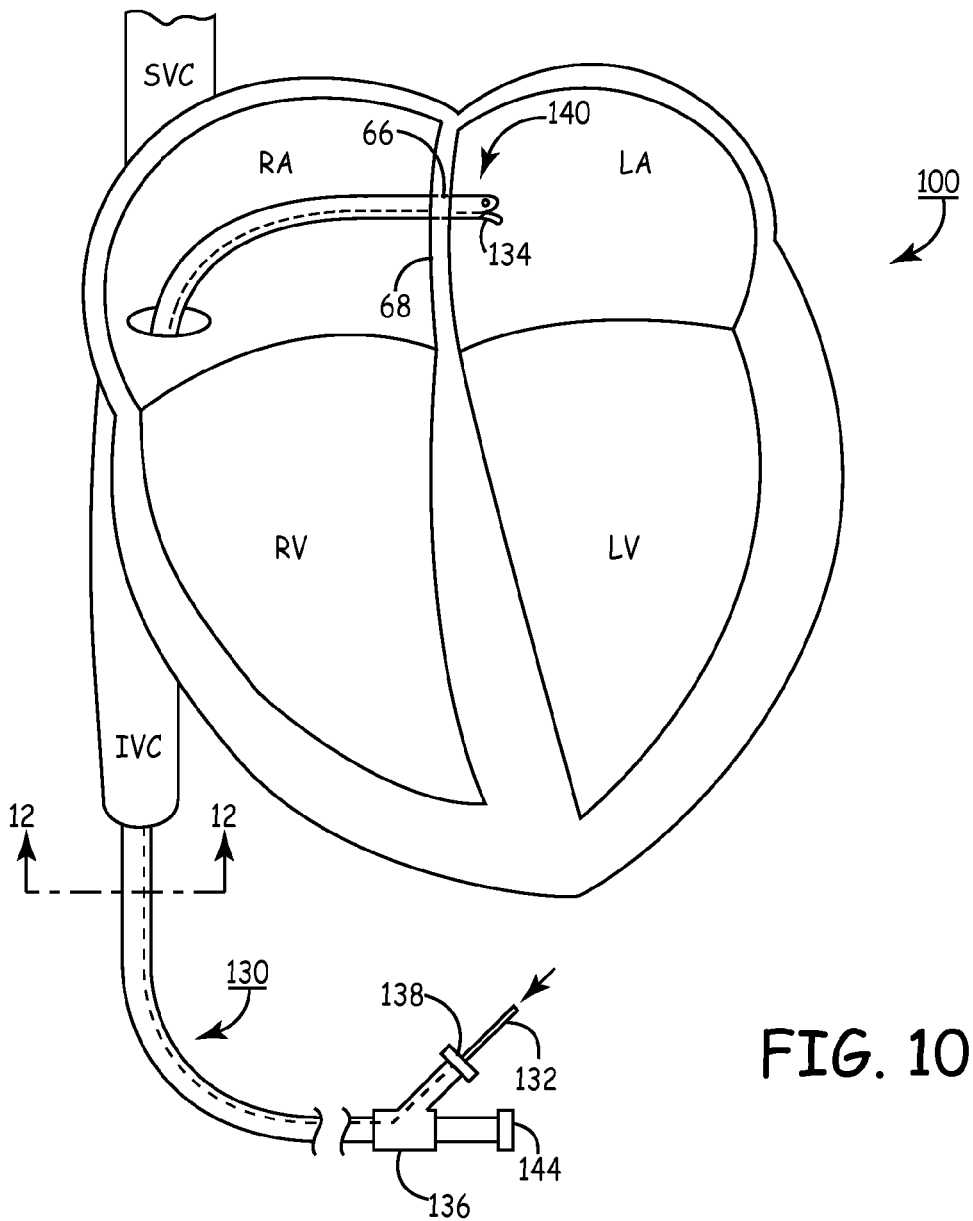
FIG. 10 is a simplified schematic illustration of the fourth embodiment of a guide catheter of the present invention showing the extendable wire that bends over when extended into the left atrium retracted into the wire deployment lumen during introduction or withdrawal of the distal segment through the septum into or from the left atrium.

FIGS. 9-11 illustrate a fourth embodiment of a guide catheter 130 of the present invention having a deployable retention mechanism that includes a distal section 134 of extendable wire 132. The distal section 134 bends over at an acute angle at bend 146 when extended from a wire lumen 138 (FIG. 12) into the LA and inhibits retraction of the guide catheter distal segment 140 into the RA by bearing against the septal wall of septum 68. The acute bend 146 in the wire 132 is straightened during advancement through the wire deployment lumen 132 as shown in FIG. 10 and by the broken lines of FIG. 11.

The retention wire 132 and wire lumen 138 can have a circular or rectangular cross-section. The retention wire 132 can be formed of a shape memory alloy and possesses superelasticity that enables straightening of the non-straight configuration within the wire deployment lumen 138.

Each of the retention wires 112 and 132 can also be formed of a non-conductive plastic material having shape memory of the non-straight configuration when released and capable of being straightened to traverse a wire deployment lumen.

It will be seen that the particular embodiments of the guide catheter can be used to guide ablation/mapping EP catheters like catheter 10 of FIGS. 1 and 2 or can be used to access the LA from the RA to introduce any other instrument or material into the LA from outside the patient's body in performance of any suitable medical procedure. It will also be understood that the guide catheters of the present invention can be employed to access the LV from the RV to introduce any other instrument or material into the LV from outside the patient's body in performance of any suitable medical procedure. Moreover, it will be apparent that such a guide catheters of the present invention can be employed to access a right heart chamber from a left heart chamber.

Each of the above-described embodiments and alternatives and equivalents thereof are used in a method of providing access through the septum separating a right heart chamber from a left heart chamber and deploying the retention mechanism into engagement with the septum to maintain the distal segment of the guide catheter extending into the heart chamber accessed by the perforation in place. The retention mechanisms are preferably located along the catheter body to be deployed or self deploy into the heart chamber that the distal segment is introduced into to inhibit retraction when retraction force is applied to the guide catheter proximal end drawing the retention mechanism against the septal wall. It will be understood that the deployment mechanisms can be deployed more proximally to the guide catheter body distal segment to bear against the septal wall when advancement force is applied to the guide catheter proximal end. Slight force can then be applied to hold the catheter in position without advancing the guide catheter further into the accessed heart chamber. Moreover, it would be possible to duplicate the retention mechanism to deploy a retention mechanism on either side of the septum.

Figure 3A:
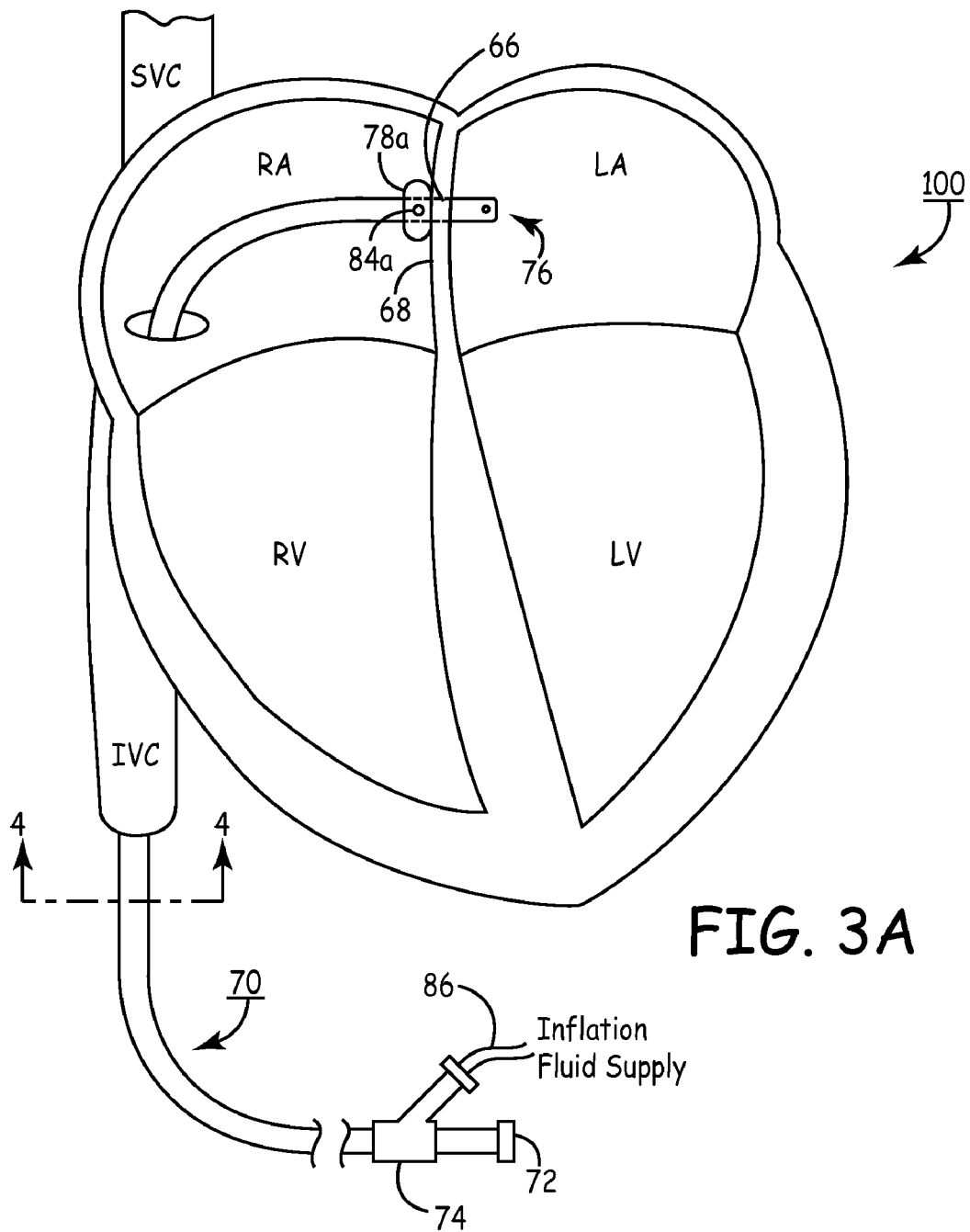
FIG. 3A is a simplified schematic illustration of an embodiment of a guide catheter of the present invention having a deployable retention mechanism comprising an expandable balloon expanded in the right atrium and pressed against the septal wall to inhibit advancement of the guide catheter distal segment into the left atrium.
Figure 3B:
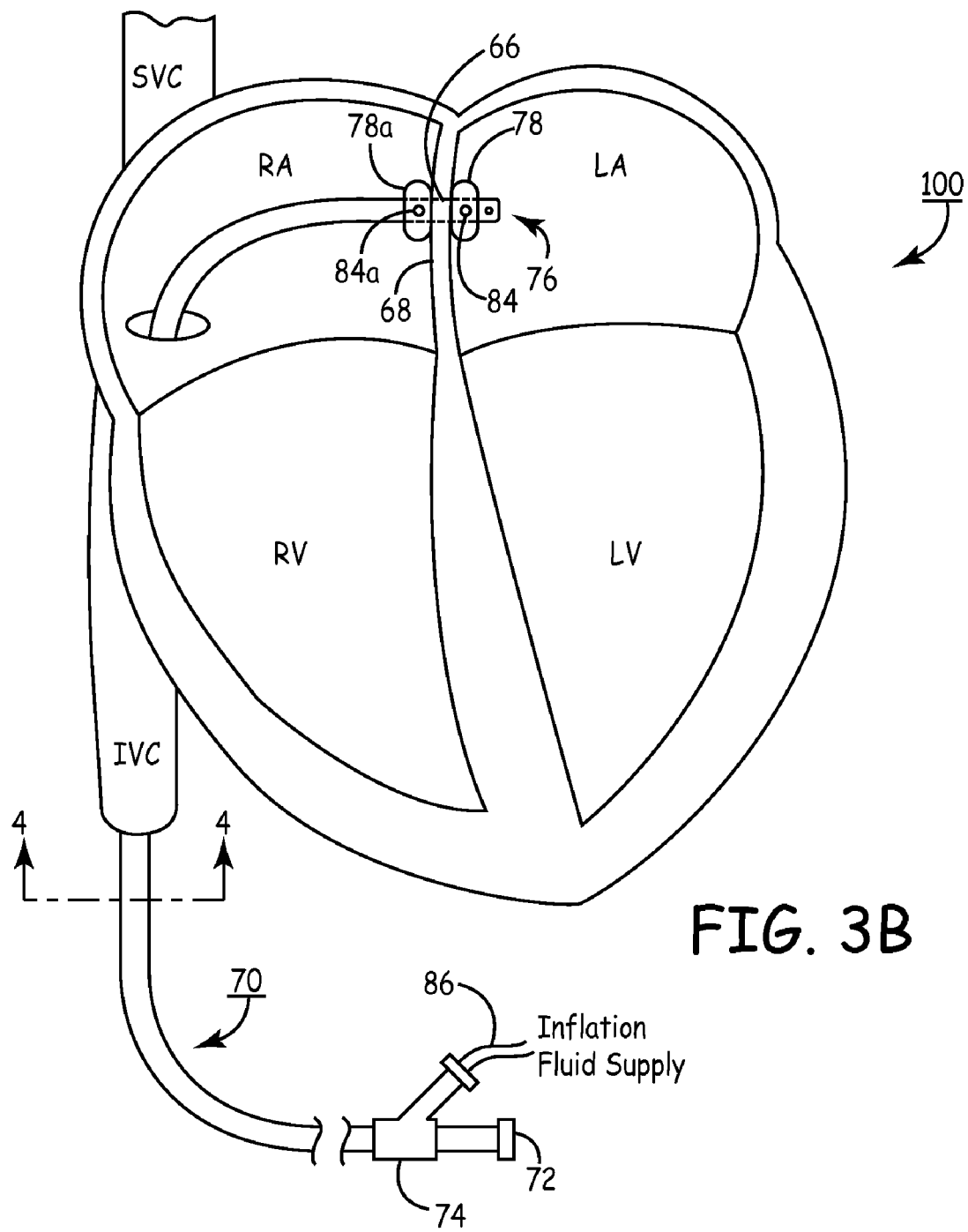
FIG. 3B is a simplified schematic illustration of an embodiment of a guide catheter of the present invention having a deployable retention mechanism comprising an expandable balloon in the right atrium and pressed against the septal wall and a balloon expanded in the left atrium and pressed against the septal wall to inhibit movement of the guide catheter distal segment.

For example, referring to the embodiment shown in FIG. 3A, the balloon 78a and port 84a can be located along the catheter body and are expanded in the RA. In another embodiment, shown in FIG. 3B, two balloons are used. Balloon 78a and port 84a can be located along the catheter body to be expanded in the RA, while balloon 78 and port 84 are located in the LA. Referring to FIGS. 5 and 6, the tines 98, 100 (and 98', 100') can be located along the catheter body to extend outward in the RA and bear against the septal wall. Or, a duplicate set of tines can be located along the catheter body to extend outward in the RA along with the depicted tines 98, 100 (and 98', 100'). Referring to FIG. 8, the wire coil 114 can be deployed from the wire deployment lumen 118 from a lumen distal end opening along the catheter body to extend outward in the RA and bear against the septal wall. Or, a duplicate wire coil can be deployed along the catheter body to extend outward in the RA along with the depicted wire coil 114. Referring to FIG. 9, the bent wire distal section 134 can be deployed from the wire deployment lumen 138 from a lumen distal end opening along the catheter body to extend outward in the RA and bear against the septal wall. Or, a duplicate bent wire distal section can be deployed along the catheter body to extend outward in the RA along with the depicted bent wire distal section 134.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A method of introducing a mapping/ablation catheter through a septum separating a first heart chamber from a second heart chamber for ablation and/or mapping of a heart wall of the second heart chamber, the method comprising the steps of:

advancing a distal segment of a guide catheter into the first heart chamber, the guide catheter including an elongated guide catheter body extending between guide catheter proximal and distal ends, the catheter body enclosing a guide catheter lumen adapted to receive the mapping/ablation catheter and including a deployable retention mechanism;

wherein the retention mechanism includes at least one flexible, pliant tine extending outwardly from a tine attachment with the distal segment of the guide catheter body to a tine free end, wherein the step of perforating and advancing includes advancing the distal segment of the guide catheter through the perforation in the septal wall such that the pliant tine is deflected inward toward the guide catheter body as the tine passes through the septal wall during passage through the perforation and extends outward when positioned in the second heart chamber;

perforating the septal wall and advancing the distal segment of the guide catheter through the perforation and into the second heart chamber;

deploying the retention mechanism into engagement against the septum within one or both of the first heart chamber and the second heart chamber when one of retraction force and advancement force is applied to the guide catheter to inhibit movement of the distal segment of the guide catheter through the septum;

introducing the mapping/ablation catheter through the guide catheter for ablation and/or mapping of the heart wall of the second heart chamber; and applying traction to the guide catheter proximal end of sufficient force to bend over the flexible pliant tine and retract the guide catheter distal segment through the perforation in the septal wall.

2. The method of claim 1, wherein the retention mechanism includes an elongated retention wire and further comprises the step of advancing the retention wire through a wire deployment lumen of the guide catheter body, disposing a distal wire segment within the second heart chamber, wherein the distal wire segment is adapted to be straightened when advanced through the wire deployment lumen and to form a non-straight configuration when extended out of the deployment lumen and into engagement with the septum within the second heart chamber, inhibiting retraction of the distal segment of the guide catheter from the second heart chamber to the first heart chamber through the septum.

3. The method of claim 2, further comprising the step of retracting the retention wire within the deployment lumen and disengaging the retention wire from the septal wall of the septum within the second heart chamber to enable retraction of the distal segment of the guide catheter into the first heart chamber through the septum.

4. The method of claim 2, wherein the non-straight configuration of the retention wire further comprises a wire coil formed of a plurality of wire turns.

5. The method of claim 2, wherein the non-straight configuration of the retention wire further comprises a wire coil formed of a plurality of wire turns wound in a common plane.

6. The method of claim 2, wherein the non-straight configuration of the retention wire further comprises an acute bend in the wire that is straightened during advancement through the wire deployment lumen.

7. The method of claim 2, wherein the retention wire is formed of a shape memory alloy and possesses superelasticity enabling straightening of the non-straight configuration within the wire deployment lumen.

8. A method of introducing a mapping/ablation catheter through a septum separating a first heart chamber from a second heart chamber for ablation and/or mapping of a heart wall of the second heart chamber, the method comprising the steps of:

advancing a distal segment of a guide catheter into the first heart chamber, the guide catheter including an elongated guide catheter body extending between guide catheter proximal and distal ends, the catheter body enclosing a guide catheter lumen adapted to receive the mapping/ablation catheter and including a deployable retention mechanism;

wherein the retention mechanism includes a first inflatable balloon and a second inflatable balloon formed about the guide catheter body at the distal segment, and further comprising the step of introducing an inflation medium through a balloon inflation and deflation lumen positioned within the guide catheter body to inflate the first inflatable balloon and the second inflatable balloon after the first inflatable balloon is advanced through the septum into the one of the first heart chamber and the second heart chamber, wherein the inflated first balloon engages the septal wall and inhibits retraction of the distal segment of the guide catheter through the septum, and the second inflated balloon engages the septum and inhibits advancement of the guide catheter through the septum;

perforating the septal wall and advancing the distal segment of the guide catheter through the perforation and into the second heart chamber;

deploying the retention mechanism into engagement against the septum within one or both of the first heart chamber and the second heart chamber when one of retraction force and advancement force is applied to the guide catheter to inhibit movement of the distal segment of the guide catheter through the septum; and introducing the mapping/ablation catheter through the guide catheter for ablation and/or mapping of the heart wall of the second heart chamber.

9. The method of claim 8, further comprising the step of evacuating the inflation medium to deflate the first balloon and the second balloon and enable one of advancement and retraction of the distal segment through the septum between the first heart chamber and the second heart chamber.

* * * * *